United States Patent [19]
Best et al.

[11] Patent Number: 6,136,565
[45] Date of Patent: Oct. 24, 2000

[54] METHODS OF REDUCING THE LEVELS OF PROTOPORPHYRIN IX IN RECOMBINANT HEMOGLOBIN PREPARATIONS

[75] Inventors: Elaine A. Best, Fort Collins, Colo.; Charles Lee Hershberger, Greenfield; Christopher Carl Frye, Mooresville, both of Ind.

[73] Assignees: Baxter Biotech Technology Sàrl, Neuchâtel, Sweden; Eli Lilly and Company, Indianapolis, Ind.

[21] Appl. No.: 09/269,584

[22] PCT Filed: Oct. 17, 1997

[86] PCT No.: PCT/US97/18950

§ 371 Date: Oct. 18, 1999

§ 102(e) Date: Oct. 18, 1999

[87] PCT Pub. No.: WO98/17809

PCT Pub. Date: Apr. 30, 1998

Related U.S. Application Data

[60] Provisional application No. 60/028,516, Oct. 18, 1996.

[51] Int. Cl.[7] .............................. C12P 21/04; C12P 21/06; C07K 14/805
[52] U.S. Cl. .................... 435/69.6; 435/69.1; 530/385
[58] Field of Search ........................... 530/385; 435/69.1, 435/69.6

[56] References Cited

U.S. PATENT DOCUMENTS 5,665,829   9/1997   Ryland et al. ........................... 530/412
5,840,851   11/1998  Plommer et al. ........................ 530/385

FOREIGN PATENT DOCUMENTS

| 90/13645 | 11/1990 | WIPO . |
| 93/09143 | 5/1993 | WIPO . |
| 95/14038 | 5/1995 | WIPO . |
| 96/15151 | 5/1996 | WIPO . |
| 98/17809 | 4/1998 | WIPO . |

OTHER PUBLICATIONS

Kazumasa Miyamoto, et al., "Isolation and Characterization of Visible Light–sensitive Mutants of *Eschericia coli* K12," Dec. 1990. pp. 393–398.

Kazumasa Miyamoto, et al., "Accumulation of protoporphyrin IX in ligh–sensitive mutants of *Escherichia coli*," Aug. 1992, pp. 246–248.

Ekaterina Kanazireva, et al., "Cloning and Overexpression of the *Rhodobacter capsulatus hemH* Gene," Jul. 1995, pp. 6693–6694.

*Primary Examiner*—Karen Cochrane Carlson
*Attorney, Agent, or Firm*—Senniger, Powers, Leavitt & Roedel

[57] ABSTRACT

The present invention relates to recombinant hemoglobin solutions containing reduced amounts of protoporphyrin IX and to methods of producing such hemoglobin solutions. The methods are accomplished by overexpressing the hemH gene in a suitable host cell or by increasing the production of hemH in a host cell, for example, by integration of the hemH gene into the chromosome of the host cell or by inserting multiple copies of the gene in host cells naturally having a hemH gene.

13 Claims, 3 Drawing Sheets

METHODS OF REDUCING THE LEVELS OF PROTOPORPHYRIN IX IN RECOMBINANT HEMOGLOBIN PREPARATIONS

This application is a national sage application of PCT/US97/18950 filed Oct. 17, 1997, which claims priority to U.S. provisional application Ser. No. 60/028 516 filed Oct. 18, 1996.

The present invention generally relates to methods of producing recombinant hemoglobin, and more particularly to methods of reducing the expression of hemoglobin containing protoporphyrin IX.

BACKGROUND OF THE INVENTION

It is not always practical or desirable to transfuse a patient with donated blood. In these situations, use of a red blood cell substitute is desirable. Such a product would need to transport oxygen, just as red blood cells do.

When patients lose blood, it is usually necessary to replace the entire fluid volume lost. However, it is not usually necessary to replace all of the lost hemoglobin. The primary goal of hemoglobin replacement therapy is to transport oxygen from the lungs to peripheral tissues. Hemoglobin administration also increases and maintains plasma volume and decreases blood viscosity. While many volume expanding colloid and crystalloid solutions are now marketed, none can transport oxygen. The only current therapy with this capability is human blood transfusion.

Genetic engineering techniques have allowed the expression of heterologous proteins in a number of biological expression systems, for example, insect cell lines, transgenic cells, yeast systems and bacterial systems. Expression of hemoglobin in particular has been demonstrated in transgenic pigs (Logan et al., WO 92/22646), yeast (De Angelo et al., WO 93/08831 and WO 91/16349; Hoffman et a., WO 90/13645), and the bacterial E. coli system (Hoffman et al., WO 90/13645). Although expression of hemoglobin in these heterologous systems can be achieved at useful levels, purification of the final product to the extreme level of purity required for practical use of hemoglobin remains difficult. Removal of contaminating isoforms of hemoglobin is particularly difficult in that these isoforms often co-purify with the desirable form of hemoglobin.

Hemoglobin (Hb) is a tetrameric protein molecule composed of two alpha and two beta globin units. Alpha and beta globin subunits associate to form two stable alpha/beta dimers, which in turn loosely associate to form the hemoglobin tetramer. Human hemoglobin Ao (also known as naturally occurring or native hemoglobin) is a heterotetramer composed of two alpha globin subunits ($a_1$, $a_2$) nd two beta globin subunits ($b_1$, $b_2$). There is no sequence difference between $a_1$ and $a_2$ or $b_1$ and $b_2$. In the unoxygenated ("deoxy", or "T" for "tense") state, the subunits form a tetrahedron. The $a_1 b_1$ and $a_2 b_2$ interfaces remain relatively fixed during oxygen binding, while there is considerable flux at the $a_1 b_2$ and $a_2 b_1$ interfaces. In the oxygenated ("oxy" or "R" or relaxed) state, the intersubunit distances are increased. The subunits are noncovalently associated by Van der Waals forces, hydrogen bonds and, for deoxy Hb, salt bridges.

In fully functional normal or native hemoglobin, a heme molecule is incorporated into each of the alpha and beta globins. Hence is a large organic molecule coordinated around an iron atom. Heme is also a cofactor in hemoglobin and is required to form soluble hemoglobin. A heme group that is lacking the iron atom is known as protoporphyrin IX (PIX) and is non-functional (cannot bind a ligand). PIX can be incorporated into one or more of the a and b subunits of hemoglobin, but the PIX-containing subunit lacks the ability to bind and release oxygen or other ligands. If all of the prosthetic groups are protoporphyrin IX rather than heme, then the hemoglobin cannot bind or release oxygen and therefore is functionless.

In E. coli and related bacteria, $heme_b$ (which is also known as "protoheme," "ferrous protoporphyrin IX" and also referred to herein as "heme") essential for respiration and for detoxification of reactive species of oxygen. $Heme_b$ serves as an essential cofactor for b-type cytochromes, catalase and peroxidase.

Biosynthesis of $heme_b$ occurs via a complex, branched pathway that involves up to twelve gene products. In non-recombinant E. coli cells, the accumulatin of large pools of heme pathway intermediates or free heme is deleterious to the cells. For example, E. coli cells with certain mutants in the gene encoding hemH are impaired in their ability to insert iron into PIX. Such hemH mutants accumulate large pools of PIX and are light sensitive. Miyamoto et al., J. Mol. Biol., 219:393–398 (1991) and Miyamoto et al., FEBS Letter, 310:246–248 (1992).

E. coli cells into which an extra copy of the hemH gene has been inserted show a decrease in the amount of PIX in the cell. Kanazireva, et al., J. of Bact., 177:6693–6694 (1995).

Because heme has a propensity to cause oxidative damage to the lipid and protein components of cellular membranes, heme is normally found associated with proteins in the cell, rather than as free heme.

The hemH locus represents the final gene in the heme biosynthesis pathway of E. coli. The gene codes for the ferrochelatase protein which is responsible for adding iron into the precursor porphyrin molecules thereby converting PIX to heme.

As discussed above, PIX incorporation produces reduced function or functionless hemoglobin. Therefore, a need exists for controlling PIX formation in recombinant hemoglobin. The present invention satisfies this need and provides related advantages as well.

SUMMARY OF THE INVENTION

The present invention relates to a method of reducing PIX-containing hemoglobin by overexpression of the hemH gene in a host cell. The methods can reduce PIX levels by at least 50% compared to the production of recombinant hemoglobin without overexpressing the hemH gene. Suitable host cells include bacterial cells, preferably E. coli. Overexpression can be achieved by insertion of a promoter which is strong enough to increase hemH gene expression such as Ptac16, Ptac17, PlacUV5 or Place(down). Ptac promoters which particularly well.

Manipulations of the hemH gene itself also increased expression of hemH. Multiple copies of the hemH gene and mutants of the hemH gene can be used for the overexpression of hemH resulting in reduced PIX. Integration of the gene into the chromosome of the host is also useful in the methods of the present invention.

The present invention is further direction to substantially PIX-free hemoglobin solutions having less than about 10% PIX-containing hemoglobin, preferably less than about 6% PIX-containing hemoglobin and most preferably less than about 1% PIX-containing hemoglobin.

DETAILED DESCRIPTION OF THE INVENTION

Figure 1:
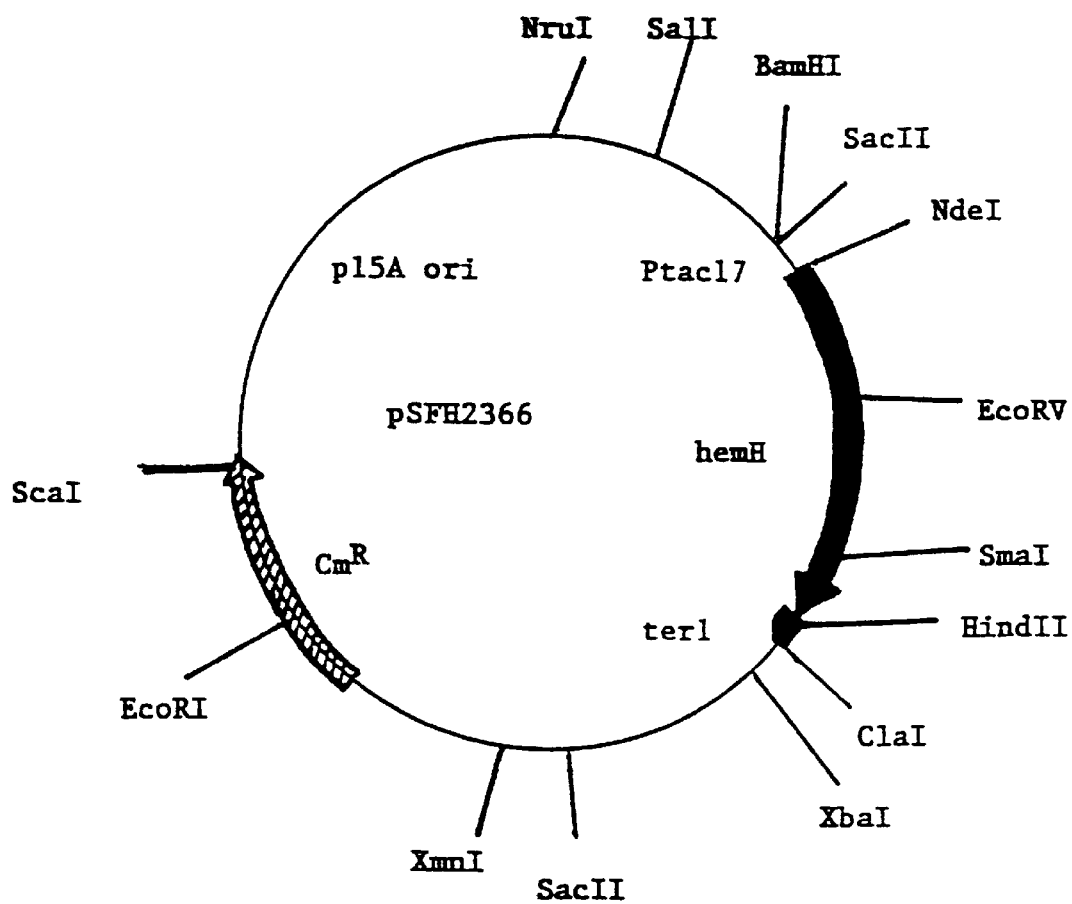
FIG. 1 shows the plasmid construct for pSFH2366 carrying the hemH gene and the Ptac17 promoter.

The present invention relates to methods of reducing PIX levels in recombinant hemoglobin solutions by overexpressing the hemH gene. These methods can be accomplished, for example, by inserting a strong promoter to drive the increased expression of the hemH gene to produce increased levels of the hemH protein. Alternatively, the methods of the present invention can be accomplished by integrating a vector containing the hemH gene and suitable operons, including a suitable promoter to drive the expression of the hemH gene, into the chromosome of a host cell. In a further embodiment, the methods can be accomplished by inserting multiple copies of the hemH gene into a host cell naturally containing a hemH gene.

As noted previously, recombinant hemoglobin expressed in bacteria, particularly *E. coli*, results in a mixture of different types of hemoglobin molecules. Although the majority of the molecules contain protoheme (ferrous protoporphyrin IX) as the prosthetic group, a smaller fraction he hemoglobin molecules incorporate PIX in place of protoheme. Hemoglobin molecules containing three or less PIX substitutions in place of protoheme have decreased thermostability than molecules containing four protoheme groups. These PIX containing hemoglobins can be selectively removed from lysate during the heat inactivation step described in WO 96/15151. Nevertheless, reduction or elimination of PIX-containing hemoglobin from the lysate prior to further purification would be advantageous.

As discussed in WO 96/15151, hemin can be supplied exogenously in producing hemoglobin from *E. coli* cells. However, it seems unlikely PIX that is incorporated into the recombinantly-produced hemoglobin is a breakdown product derived from the exogeneous source. It is believed that the PIX contamination is synthesized by the *E. coli* host bacterium.

Two pathways for PIX formation are possible. Both of these pathways are predicted to require the enzyme ferrochelatase, which is encoded by the hemH gene. Ferrochelatase, encoded by the hemH gene, catalyzes the insertion of iron into PIX to form heme. The sequence of the hemH gene is also disclosed in Miyamoto et al., *J. Mol. Biol.*, 219:393–398 (1991). Protein sequences of ferrochelatases have confirmed that the sequences are well conserved in many species. *E. coli* ferrochelatase shows a 51% identity at the amino acid level to Hemophilus influenzae ferrochelatase and 43% identity to ferrochelatase from *Bradyrhizobium japoncium*, gram-negative bacteria, and 23% identity to ferrochelatase from the gram-positive bacterium *Bacillus subtilis*.

In one pathway ("forward reaction"), PIX accumulates because conversion of the *E. coli*-produced PIX to protoheme by ferrochelatase is a slow reaction. In the alternative pathway, ferrochelatase catalyzes the removal of iron from protoheme, which can be produced by the cell or supplied exogeneously, resulting in accumulation of PIX ("reverse reaction"). It was speculated that if the "forward reaction" is the source of the PIX, then one would expect overexpression of hemH to decrease the intracellular pool of PIX and to reduce the level of contaminating PIX-containing hemoglobin species. Conversely, if the "reverse reaction" is the source of the PIX, then overexpression of hemH is predicted to increase levels of PIX and PIX-containing hemoglobin.

*E. coli* strains that express recombinant hemoglobin, particularly rHb1.1 (pSGE72), and various levels of ferrochelatase were constructed. The details of the strain production are detailed in the Examples below. The results surprisingly showed the PIX is generated b the "forward reaction" and that he overexpression of hemH is a useful method for reducing PIX-hemoglobin species.

The present invention therefore relates to the surprising discovery that overexpressing the hemH gene, which is the final step in the heme biosynthetic heme pathway, results in less PIX-containing hemoglobin. Methods of reducing PIX-containing hemoglobin are therefore provided. The present invention further relates to essentially protoporphyrin IX-free hemoglobin solutions and pharmaceutical compositions obtained by the methods of the present invention.

To assist in the interpretation of the resent patent, the following terms shall have the following meaning throughout this patent:

"Hemoglobin" or "hemoglobin-like protein" comprises one or more heterotertramers composed of (a) two alpha globin-like and two beta globin-like polypeptides, (b) one di-alpha globin-like and two beta globin-like polypeptides, (c) two alpha globin-like and one di-beta globin-like polypeptide, (d) one di-alpha globin-like and one di-beta globin-like polypeptides, (e) one fused alpha/beta globin-like polypeptide and separate alpha and beta globin-like polypeptides, or (f) two fused alpha/beta globin-like polypeptides. A polypeptide of one tetramer may be crosslinked or genetically fused to a polypeptide of another tetramer. A hemoglobin is said to be multimeric if it comprises more than four globin subunits or domains. The term "multimeric" thereby includes octameric hemoglobin (2 linked tetramers), as well as higher multimers. In hemoglobin or hemoglobin-like protein, whether derived from natural or recombinant sources, in either the R or the T state, each alpha and beta globin-like polypeptide may contain a heme or protoporphyrin IX prosthetic group and therefore may have the ability to bind oxygen.

"Recombinant hemoglobin" means hemoglobin comprising alpha-like globin polypeptides and beta-like globin polypeptides at least one of which is obtained by expression of a globin gene carried by a recombinant DNA molecule, whether the hemoglobin is a conventional hemoglobin or a mutant species, resulting in expression of a hemoglobin gene to produce a hemoglobin protein in a cell other than a cell in which such hemoglobin gene and/or hemoglobin protein is naturally found, i.e., the hemoglobin gene is heterologous to the host in which it is expressed. Therefore, the expression of any human hemoglobin gene in any cell other than a human red blood cell would be considered to be a recombinant hemoglobin, such as bacteria, yeast, non-human erthyrocyte mammalian cells and insects. Moreover, the expression of a vertebrate hemoglobin an any species of invertebrate, or any vertebrate cell other than the vertebrate cell where the hemoglobin to be expressed is naturally occurring, would be considered a recombinant hemoglobin. Additionally, the expression of any naturally occurring hemoglobin mutant in any species other than the species in which it is naturally occurring, would be considered a recombinant hemoglobin. The expression of any non-naturally occurring mutant hemoglobin in any species would be considered a recombinant hemoglobin.

"Liganded hemoglobin" means hemoglobin having at least one heme prosthetic group to which any ligand is bound. Common ligands include, but are not limited to, $O_2$, $CO_2$, NO, CO, HCN, and the like. Preferably the ligand is one that binds the heme pocket. Common preferred ligands include, but are not limited to, $O_2$, CO, NO and the like.

"Oxyhemoglobin" means hemoglobin in which each of the functional oxygen binding sites has bound to it an oxygen molecule.

"Deoxyhemoglobin" or "unliganded hemoglobin" means any hemoglobin to which not ligand is bound to the alpha globin, the beta globin, and/or any functional heme prosthetic group.

"Protoporphyrin IX-containing hemoglobin" means any hemoglobin in which one or more heme prosthetic groups does not contain an iron atom.

"R-state hemoglobin" is the high affinity state of hemoglobin and is the dominant form of hemoglobin when a ligand is bound at the heme pockets. The ligand is typically oxygen, thus this state is known as the "oxy" or "R" (for relaxed) state. In the R state, intersubunit distances are increased relative to the distances in T-state hemoglobin.

"T-state hemoglobin" means the unoxygenated ("deoxy", or "T" or "tense") state, in which the subunits form a tetrahedron. The $a_1b_1$ and $a_2b_2$ interfaces remain relatively fixed during oxygen binding, while there is considerable flux a the $a_1b_2$ and $a_2b_1$ interfaces.

"rHb1.1" means one di-alpha-like globin and two beta-like globins, wherein the two alpha-like globins are connected by a single glycine between the C terminus of a first alpha-like globin and the N terminus of a second alpha-like globin, the beta-like globins contain the Presbyterian mutation, bN108→K, and the first alpha-like globin and the beta globins contain a val→met mutation at the N terminus.

"Substantially PIX-free hemoglobin" relates to insignificant levels of protoporphyrin IX-containing hemoglobin in a hemoglobin solution are those levels of protopoophyrin IX-containing hemoglobin that do not adversely affect the suitability and/or activity for a particular utility. Preferably, the amount of protoporphyrin IX-containing hemoglobin in a hemoglobin solution is less than about ten percent (10%) of the total hemoglobin, more preferably, less than about six percent (6%) of the total hemoglobin, more preferably less than about one percent (1) of the total hemoglobin. Most preferably, the protoporphyrin IX-containing hemoglobin in a hemoglobin solution is below the detection limit for protorporphyrin IX in a given measurement technique as described, for example, in the examples below (i.e., a detection limit of about 0.4%).

General methods for making recombinant hemoglobin are now well know. The genes encoding subunits of a desired hemoglobin may be cloned, placed in a suitable expression vector and inserted into an organism, such as a microorganism, animal or plant, or into cultured animal or plant cells or tissues. These organisms may be produced using standard recombinant DNA techniques. Human alpha and beta globin genes have been cloned and sequenced by Liebhaber et al., Porc. Natl. Acad. Sci. USA (1980) 77;7054–7058 and Marotta et al., Journal of Biological Chemistry (1977) 252; 5040–5053, respectively. Techniques for expression of both wild-type and mutant alpha and beta globins, and their assembly into a hemoglobin, are set forth in U.S. Pat. NO. 5,028,588 to S. J. Hoffman, and K. Nagai and Hoffman, S. J. et al., PCT/US90/02654, Townes, T. M. and McCune, S. L., PCT/US91/09624, and De Angelo, J. et al., PCT/US91/02568 and PCT/US91/08108 and European Patent Application 87116556.9 and PCT/US90/02654, all incorporated herein by reference.

Ferrochelatase mutants are also useful in the present invention. For example, the hemH225 mutation changes threonine-15 to methionine. Those skilled in the art can readily determine other hemH mutants that are useful following he guidance provided herein.

Derivatives of *E. coli* strain SGE1464 containing pSFH2367 (SGE2885), a pACYC184-derived plasmid in which the *E. coli* hemH gene is expressed from the *E. coli* placUV5 promoter, produced half as much PIX rHb1.1 as a control strain (SGE1464) in 15 liter fermentation tests as shown in Table 1 below. This surprising 50% reduction in PIX-containing hemoglobin species results in a significant improvement in the yield of PIX-free hemoglobin. For example, reducing PIX from 6.56% to 3.30% results in approximately 12% improvement in PIX-free hemoglobin. Preferably, the substantially PIX-free hemoglobin solution contains less than about 10% PIX, more preferably less than about 6% PIX, and most preferably less than about 1% PIX.

TABLE 1

Effect of hemH overexpression on ferrochelatase, % PIX and soluble rHb1.1

| Strain | Features | Trials | Soluble Ferrochelatase Activity (U/mg) | Soluble rHb1.1 (g/liter) | % PIX |
|---|---|---|---|---|---|
| SGE1464 | pSGE720 | 2 | 1.74 | 1.15 | 6.56 |
| SGE2885 | pSGE720+ | 7 | 23.20(±2.92) | 1.05 (±0.08) | 3.30(±0.09) |

Strains were designed to co-express the HemH protein at a level that would reduce PIX levels without negatively impacting rHb1.1 potency. For the episomal study using the pACYC184-based vector backbone, a series of promoters were inserted with varying transcriptional strength. These strains were analyzed for ferrochelatase activity using a zinc-mesoporphyrin assay as described in Example 4. The results of the study showed a correlation between increased levels of zinc product (zinc mesopoorphyrin) as promoter strenth increased as follows: Ptac16>Ptac17>PlacUV5>Plac>Plac(down).

Preferably, useful plasmids are designed to allow the integration of the hemH gene (under the control of various promoters) into a desired expression host's chromosome. This integratino can be accomplished using pMAK705-based derivatives. The Integration was "targeted" to the galE locus of *E. coli*, thus integrants would carry the gal-phenotypte. Integrated strains were subsequently evaluated in the fermentors and shown to reduce the amount of globin containing PIX by nearly 40%, without negatively impacting rHb1.1 potency.

In a further embodiment of the resent invention, multiple copies of the hemH gene can be inserted into a desired host cell to increase the production of the hemH protein. Any conventional method or other methods known to those skilled in the art can be used to insert such multiple copies.

The substantially protoporphyrin IX free hemoglobin solution produced can then be subjected to further purification techniques that are known in the art to further remove other hemoglobin and non-hemoglobin contaminants from the substantially protoporphyrin IX free hemoglobin solution to result in a hemoglobin solution that is very pure. The techniques for further purification can be, for example, as described in WO 96/15151, incorporated herein by reference.

The substantially PIX-free recombinant hemoglobin of the present invention can be used for a number of in vitro or in vivo applications. Such in vitro applications include, for example, the delivery of oxygen by compositions of the instant invention for the enhancement of cell growth in ell culture by maintaining oxygen levels in vitro (DiSorbo and Reeves, PCT publication WO 94/22482, herein incorporated by reference). Moreover, the hemoglobins of the instant invention can be used to remove oxygen from solutions requiring the removal of oxygen (Bonaventura and Bonaventura, U.S. Pat. No. 4,343,715, incorporated herein by reference) and as reference standards for analytical assays and instrumentation (Chiang, U.S. Pat. No. 5,320,965, incorporated herein by reference) and other such in vitro applications known to those of skill in the art.

In a further embodiment, the substantially PIX-free hemoglobins of the present invention can be formulated for use in therapeutic applications. Example formulations suitable for the hemoglobin of the instant invention are described in Milne, et al., WO 95/14038 and Gerber et al., PCT/US95/10232, both herein incorporated by reference. Pharmaceutical compositions of the invention can be administered by, for example, subcutaneous, intravenous, or intramuscular injection, topical or oral administration, large volume parenteral solutions useful as blood substitutes, etc. Pharmaceutical compositions of the invention can be administered by an conventional means such as by oral or aerosol administration, by transdermal or mucus membrane adsorption, or by injection.

For example, the hemoglobins of the present invention can be used in compositions useful as substitutes for red blood cells in any application that red blood cells are used or for any application in which oxygen delivery is desired. Such hemoglobins of the instant invention formulated as red blood cell substitutes can be used for the treatment of hemorrhages, traumas and surgeries where blood volume is lost and either fluid volume or oxygen carrying capacity or both must be replaced. Moreover, because the hemoglobins of the instant invention can be made pharmaceutically acceptable, the hemoglobins of the instant invention can be used not only as blood substitutes that deliver oxygen but also as simple volume expanders that provide oncotic pressure due to the presence of the large hemoglobin protein molecule. In a further embodiment, the hemoglobin of the instant invention can be crosslinked by methods known in the art and used in situations where it is desirable to limit the extravasation or reduce the colloid osmotic pressure of the hemoglobin-based blood substitute. Thus the hemoglobins of the instant invention can act to transport oxygen as a red blood cell substitute, while reducing the adverse effects that can be associated with excessive extravasation.

A typical does of the hemoglobins of the instant invention as an oxygen delivery agent can be from 2 mg to 5 grams or more of extracellular hemoglobin per kilogram of patient body weight. Thus, a typical does for a human patient might be from a few grams to over 350 grams. It will be appreciated that he unit content of active ingredients contained in an individual does of each dosage form need not in itself constitute an effective amount since the necessary effective amount could be reached by administration of a plurality of administrations as injections, et. The selection of dosage depends upon the dosage form utilized, the condition being treated, and the particular purpose to be achieved according to the determination of the skilled artisan in the field.

Administration of the hemoglobins of the instant invention can occur for a period of seconds to hours depending on the purpose of the hemoglobin usage. For example, as an oxygen delivery vehicle, the usual time course of administration is as rapid as possible. Typical infusion rates for hemoglobin solutions as blood replacements can be from about 100 ml to 300 ml/hour.

In a further embodiment, the hemoglobins of the instant invention can be used to treat anemia, both by providing additional oxygen carrying capacity in a patient that is suffering from anemia, and/or by stimulating hematopoiesis as described in PCT publication WO 95/24213. When used to stimulate hematopoises, administration rates can be slow because the dosage of hemoglobin is much smaller than dosages that can be required to treat hemorrhage. Therefore the hemoglobins of the instant invention can be used for applications requiring administration to a patient of high volumes of hemoglobin as well as in situations where only a small volume of the hemoglobin of the instant invention is administered.

Because the distribution in the vasculature of the hemoglobins of the instant invention is not limited by the size of the red blood cells, the hemoglobin of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation, any tissues that are suffering from oxygen starvation or are hypoxic, and the like. Additionally, any type of tissue ischemia can be treated using the hemoglobins of the instant invention. Such tissue ischemias include, for example, stroke, emerging stroke, transient ischemica attacks, myocardial stunning and hibernation, acute or unstable angina, emerging angina, infarct, and the like. Because of the broad distribution in the body, the hemoglobins of the instant invention can also be used to deliver drugs and for in vivo imaging.

The hemoglobins of the instant invention can also be used as replacement for blood tat is removed during surgical procedures where the patient's blood is removed and saved for reinfusion at the end of surgery or during recovery (acute normovolemic hemodilution or hemoaugmentation). In addition, the hemoglobins of the instant invention can be used to increase the amount of blood that can be predonated prior to surgery, by acting to replace some of the oxygen carrying capacity that is donated.

The following examples are intended to illustrate, but not limit, the present invention.

EXAMPLES

Example 1

Method of Measuring Proptoporphyrin IX Content in a Crude Protoporphyrin IX-Containing Hemoglobin Solution The determination of the protoporphyrin IX (PIX) content in hemoglobin samples are accomplished by HPLC (high performance liquid chromatography) analysis based on the separation of heme and protoporphyrin IX from globin on a reversed phase column. Samples are diluted to approximately 1mg/ml hemoglobin prior to analysis. To ensure that all heme compounds are quantitated with the same color factor, all heme in the solution are oxidized to hemin before analysis. This oxidation is accomplished by mixing $K_3[Fe(CN_6)]$ with the hemoglobin sample just before injection of the sample onto the column to oxidize $Fe^{2+}$ in heme to $Fe^{3+}$. Elution of heme, protoporphyrin IX, and globins is accomplished by an increasingly nonpolar buffer gradient (e.g., water/TFA to acetonitrile). Spectra of hemin and protoporphyrin IX is similar, with absorption maxima at 398 nm and 405 nm, respectively. At 396 nm, color factors for heme and protoporphyrin IX are almost equal, therefore the areas under each pack correspond directly to the relative content of each component. Levels of proptoporphyrin IX less than 0.4% (proptoporhyrin IX/heme+protoporphyrin IX) are considered to lie below the detection limit of preferred analytical methodologies. Spectral measurements can be made anywhere in the range of about 390–410 nm with similar results.

Example 2
Episomal Hemoglobin Expression

Hemoglobin was produced as essentially described in WO 96/15151, incorporated herein by reference, with modifications necessary to overexpress the hemH gene. Those skilled in the art can readily determine the modifications needed to produce the strains in which the enzyme ferrochelatase is overexpressed. The vectors us to produce the hemoglobins included the following:

The pSGE720 plasmid is described in WO 97/04110. Plasmid pSFH2337 contains the hemH gene in pACYC184 background with expression driven by the Ptac 16 promoter. It was constructed subcloning expression cassette form the plasmid pSGE590 as Ban HI/ClaI fragment into pACYC184 (ATCC 37033). This construct does not contain an upstream, but does have a downstream transcriptional terminator. The Ptac 17 promotor was cloned via BamHI/NdeI adaptor into pSFH2337 (pACYC184/hemH based) backbone driving HemH expression to construct the pSFH2366 plasid (FIG. 1). Plasmids pSFH2367, pSFH2368, and pSFH2369 were similarly cloned via the BamHI/NdeI adaptor into pSFH2337, but with the PlacUV5 promoter, Plac promoter, and Plac(down) promoters, respectively. The cloning variables are shown in FIG. 2.

B. Integration Protocol

The desired plasmid (pMAK705) was transformed into the desired strain according to conventional methods and grown overnight at 30° C. under antibiotic selection. The resulting culture was dilutd back to $OD_{600}$=0.05 and grown to an $OD_{600}$=0.2. The culture was then dilutd to $10^{-3}$, $10^{-4}$ and $10^{-5}$ and plated 100 μL onto L agar with the appropriate antibiotic selection. The plated cultures were grown overnight at 44° C. single colonies were picked and grown at 30° C. with selection overnight (excision). The cultures were subcultured and grown at 44° C. with no selection (curing) with continued subculturing for three passages. Single colonies were selected by streaking on L agar (no selection). Each colony was patched on L agar with selection and without selection to confirm curing. The colonies were then screened for the desired phenotype.

Figure 2:
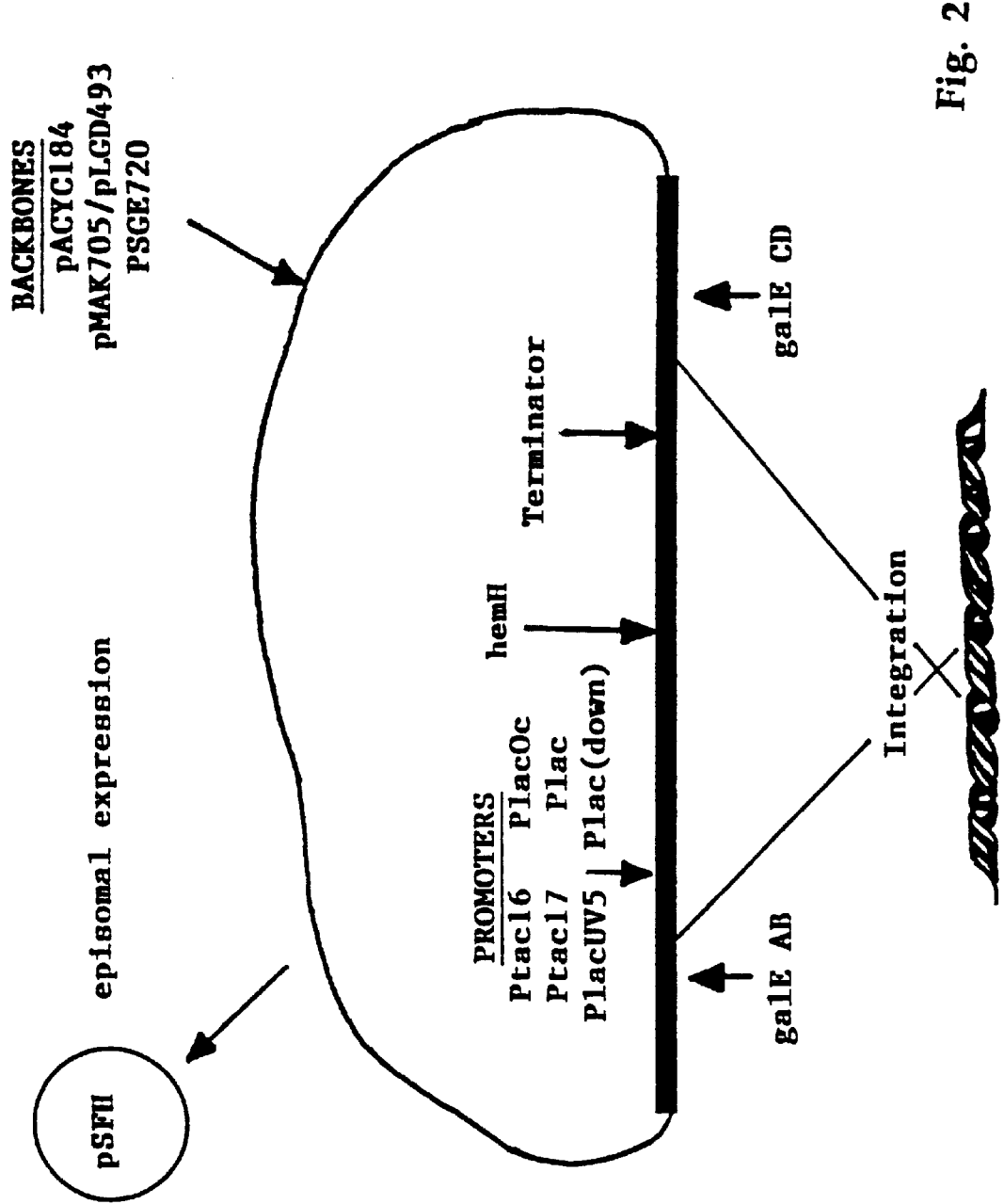
FIG. 2 shows the construction variables used for the episomal and chromosomal integration studies.
Figure 3:
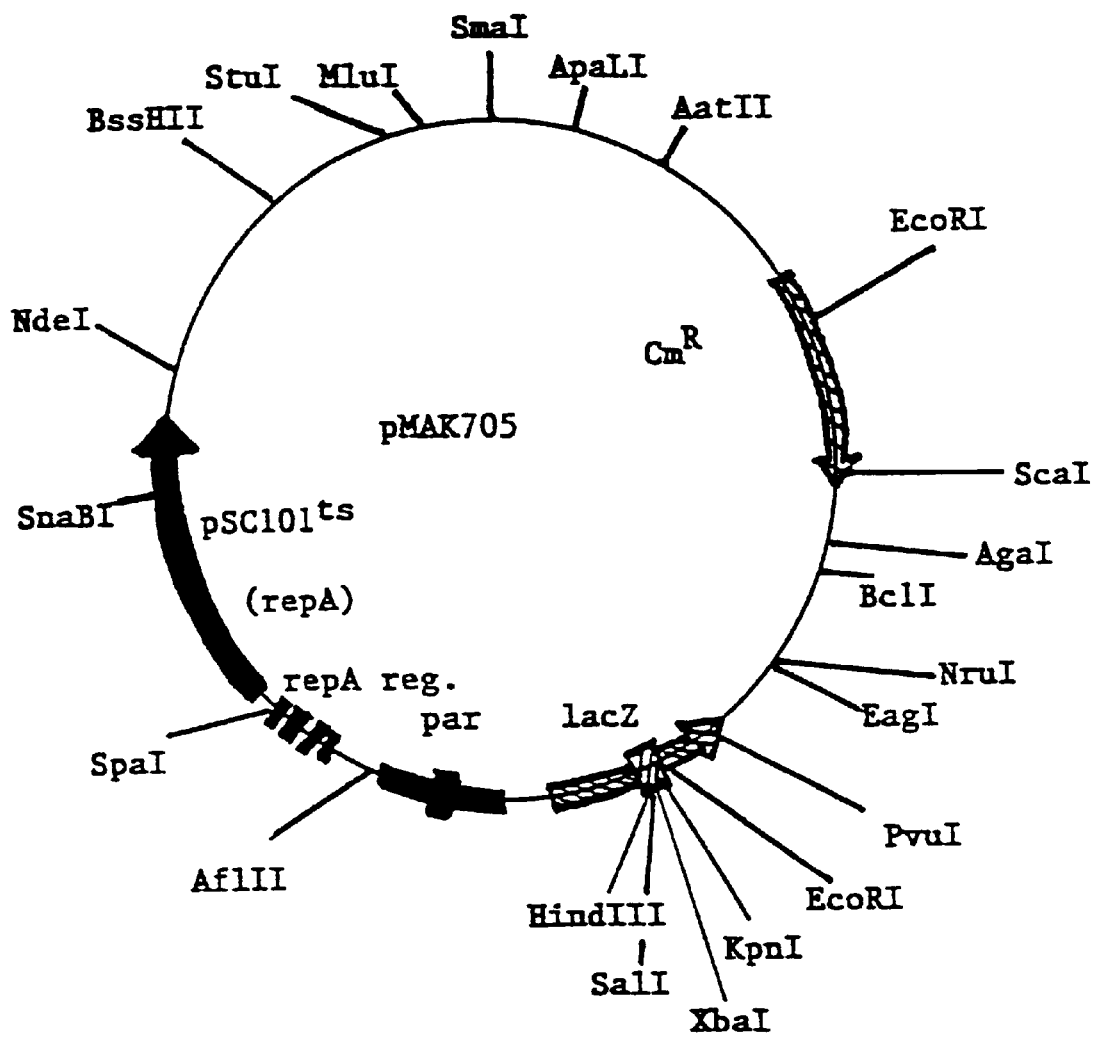
FIG. 3 shows the plasmid construct for pMAK705.

The construction variants for the integration are shown in FIG. 2. Genetic constructs of the proposed integrants were confirmed by PCR analysis.

Results

| Strain | Promotor | Zn Product (μg/mL) | Zn Product/ $OD_{600}$ |
| --- | --- | --- | --- |
| pSGE720/.17 | NA | 9 | 0.973 |
| pSFH2337/pSGE720 | Ptac16 | 402 | 50.9 |
| pSFH2366/pSGE720 | Ptac17 | 246 | 31.9 |
| pSFH2367/pSGE720 | PlacUV5 | 117 | 13.7 |
| pSFH2368/pSGE720 | Plac | 68 | 8.7 |
| pSFH2369/pSGE720 | Plac(down) | 78 | 8 |

Example 4
Ferrochelatase Assay

The following reverse phase HPLC (RP-HPLC) parameters were used to conduct the ferrochelatase assay:

A) Mobile Phase
1) Mobile phase A (0.1 M ammonium acetate, pH 5.15+/− 0.03, 2 liter volume)
2) Mobile Phase B (50% methanol:50% acetonitrile, 2 liter volume)

B) Equipment
1) Chilled (5–10° C.) automatic injector with a variable loop capable of 20–100 μL volume, or a suitable syringe injector. Injection volume of quenched reaction=100 μL.
2) Gradient HPLC system that can produce a flow rate to 1.0–1.2 ml/min.
3) Guard column—Betasil C8 drop-in guard columns (Keystone Scientific).
4) Analytical column—Betasil C8 (150 mm×4.6 mm ) (Keystone Scientific)
5) UV detector set at 399 nm
6) Gradient event list:

| Time[min] | % B |
| --- | --- |
| 0.0 | 60 |
| 20 | 80 |
| 21 | 60 |
| 25 | END |

Not: Gradient slop should not be altered. The initial percentage of buffer B may be adjusted to obtain a retention time of 600–900 seconds for Zn mesoporphyrin peak.

7) Column oven set at 50° C.

In the assay, 1 ml cell pellet was added to 1ml 50 mM Tris and DTT (pH 8.0) and sonicated for 60 seconds to lysis the cells. The sonicated material was then centrifuged to recover the cell extract. The cell extract (ferrochelatae) was added to $Zn^{+2}$ and mesoporphyrin under aerobic conditions at 37° C. for 10 minutes to form Zn mesoporphyrin and subsequently quenched with EtOH/EDTA/DMSO to allow the analysis of Zn mesoporphyrin by RP-HPLC. The advantages of using this assay included (1) the reaction does not require anerobic conditions because Zn is in the preferred valence of +2; (2) a reaction time of 10 minutes at 37° C.; (3) samples run in duplicate showed good reproducibility; (4) sample load capacity increased from 5 to 30 samples/day; (5) the reaction was quenched with ethanol, EDTA and DMSO and, therefore, did not require any hazardous chemicals; and (6) increased sensitivity by detection with 20 minute RP-HPLC.

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

What is claimed is:

1. A method of reducing protoporphyrin IX (PIX)-containing hemoglobin in the production of recombinantly produced hemoglobin, said method comprising inserting a promoter into a host cell expressing exogenous hemoglobin, wherein said promoter causes an increase in the expression of the hemH gene.

2. The method of claim 1, wherein the promoter is Ptac 16, Ptac 17, Plac, PlacUV5, or Plac(down).

3. The method of claim 2, wherein the promoter is Ptac 16 or Ptac 17.

4. A method of reducing protoporphyrin IX (PIX)-containing hemoglobin in the production of recombinantly produced hemoglobin, said method comprising inserting multiple copies of the hemH gene into a host cell expressing exogenous hemoglobin, wherein said hemH genes are expressed therein.

5. The method of claim 4, wherein a cop of the hemH gene is integrated into the chromosome of said host cell.

6. The method of claim 5, wherein the hemH gene is integrated into the chromosome of an *E. coli* host cell expressing exogenous hemoglobin, wherein said integration is at or near the galE locus of *E. coli*.

7. The method of claim 1 or claim 4, wherein the host cell is a bacterial host cell.

8. The method of claim 1 or claim 4, wherein the host cell is *E. coli*.

9. The method of claim 1 or claim 4, wherein said PIX-containing hemoglobin is reduced by at least 50% when compared to the production of recombinant hemoglobin without increased expression of the hemH gene.

10. The method of claim 1 or claim 4, wherein said PIX-containing hemoglobin is reduced to less than 10% when compared to the production of recombinant hemoglobin without increased expression of the hemH gene.

11. The method of claim 1 or claim 4, wherein said PIX-containing hemoglobin is reduced to less than 6% when compared to the production of recombinant hemoglobin without increased expression of the hemH gene.

12. The method of claim 1 or claim 4, wherein said PIX-containing hemoglobin is reduced to less than 1% when compared to the production of recombinant hemoglobin without increased expression of the hemH gene.

13. The method of any one of claims 2 to 12, wherein the exogenuous hemoglobin is a hemoglobin mutant having a reduced oxygen affinity when compared to native hemoglobin $A_o$.

* * * * *